US012806226B2

(12) United States Patent
Shah

(10) Patent No.: US 12,806,226 B2
(45) Date of Patent: Nov. 24, 2026

(54) PROPHYLAXIS AND THERAPY FOR OCULAR DISEASES LEADING TO BLINDNESS

(71) Applicant: Kumarpal A. Shah, Searingtown, NY (US)

(72) Inventor: Kumarpal A. Shah, Searingtown, NY (US)

( * ) Notice: Subject to any disclaimer, the term of this patent is extended or adjusted under 35 U.S.C. 154(b) by 299 days.

(21) Appl. No.: 18/506,725

(22) Filed: Nov. 10, 2023

(65) Prior Publication Data

US 2025/0152620 A1 May 15, 2025

(51) Int. Cl.
*A61K 31/795* (2006.01)
*A61K 45/06* (2006.01)
*A61P 27/02* (2006.01)

(52) U.S. Cl.
CPC ............ *A61K 31/795* (2013.01); *A61K 45/06* (2013.01); *A61P 27/02* (2018.01)

(58) Field of Classification Search
CPC ........ A61K 31/795; A61K 45/06; A61P 27/02
See application file for complete search history.

(56) References Cited

U.S. PATENT DOCUMENTS 3,987,163 A * 10/1976 Rankin ................ A61K 9/0048 424/78.04
8,268,310 B2 9/2012 Hass et al.
8,753,625 B2 6/2014 Fung et al.
10,426,773 B2 10/2019 Palczewski et al.
11,274,307 B2 3/2022 Erickson et al.
2016/0317573 A1* 11/2016 Shah ...................... A61K 9/146

FOREIGN PATENT DOCUMENTS

CN 101091926 A * 12/2007

OTHER PUBLICATIONS

Lombardo et al. (Challenges in Age-Related Macular Degeneration: From Risk Factors to Novel Diagnostics and Prevention Strategies), Frontiers in Medicine, vol. 9, Jun. 2022.*

Mauck et al., (Single and multiple exposure tolerance study of polystyrene sulfonate gel: a Phase I safety and colposcopy study), Contraception 70 (2004) 77-83.*

Ackland P et al, World blindness and visual impairment: despite many successes, the problem is growing. Community Eye Health. 2017;30(100):71-73, [on-line], [retrieved Nov. 25, 2023]. Retrieved from the Internet <URL: https://www.ncbi.nlm.nih.gov/pmc/articles/PMC5820628/>.

Armitage WJ et al, High-risk Corneal Transplantation: Recent Developments and Future Possibilities. Transplantation. Dec. 2019;103(12):2468-2478, [on-line], [retrieved Nov. 25, 2023]. Retrieved from the Internet <URL: https://pubmed.ncbi.nlm.nih.gov/31765363/> <doi: 10.1097/TP.0000000000002938>.

Cao H et al, Risk factors for acute endophthalmitis following cataract surgery: a systematic review and meta-analysis. PLoS One. Aug. 26, 2013;8(8):e71731, [on-line], [retrieved Nov. 25, 2023]. Retrieved from the Internet <URL: https://www.researchgate.net/publication/256291949_Risk_Factors_for_Acute_Endophthalmitis_following_Cataract_Surgery_A_Systematic_Review_and_Meta-Analysis> <doi: 10.1371/journal.pone.0071731>.

Clark SJ et al, The eye as a complement dysregulation hotspot. Semin Immunopathol. Jan. 2018;40(1):65-74, [on-line], [retrieved on Nov. 25, 2023]. Retrieved from the Internet <URL: https://pubmed.ncbi.nlm.nih.gov/28948331/> <doi: 10.1007/s00281-017-0649-6>.

Gibson BG et al, Contribution of animal models to the mechanistic understanding of Alternative Pathway and Amplification Loop (AP/AL)-driven Complement-mediated Diseases. Immunol Rev. Jan. 2023;313(1):194-216 [on-line], [retrieved on Nov. 25, 2023]. Retrieved from the Internet <URL: https://onlinelibrary.wiley.com/doi/pdf/10.1111/imr.13141> <doi: 10.1111/imr.13141>.

Harrison RA et al, The complement alternative pathway in health and disease-activation or amplification? Immunol Rev. Jan. 2023;313(1):6-14, [on-line], [retrieved on Nov. 25, 2023]. Retrieved from the Internet <URL: https://onlinelibrary.wiley.com/doi/10.1111/imr.13172> <doi: 10.1111/imr.13172>.

Jha P et al, The role of complement system in ocular diseases including uveitis and macular degeneration. Mol Immunol. Sep. 2007;44(16):3901-8, [on-line], [retrieved on Nov. 25, 2023]. Retrieved from the Internet <URL: https://www.ncbi.nlm.nih.gov/pmc/articles/PMC2045508/pdf/nihms-29945.pdf> <doi: 10.1016/j.molimm.2007.06.145>.

Dreismann AK et al, Gene targeting as a therapeutic avenue in diseases mediated by the complement alternative pathway. Immunol Rev. Jan. 2023;313(1):402-419, [on-line], [retrieved on Dec. 5, 2023]. Retrieved from the Internet <URL: https://www.researchgate.net/publication/365323080_Gene_targeting_as_a_therapeutic_avenue_in_diseases_mediated_by_the_complement_alternative_pathway/link/636fd127431b1f5300926784/download> <doi: 10.1111/imr.13149>.

(Continued)

*Primary Examiner* — Zohreh A Fay
(74) *Attorney, Agent, or Firm* — Keusey & Associates, P.C.

(57) ABSTRACT

A method for prophylaxis and therapy of blindness to addresses the unmet medical needs in the ophthalmic branch of medicine. Most specifically, the invention details a method to block complement mediated hyper activation that contributes to inflammation in host ocular tissues. The complement mediated inflammation in various structures of eyes such as sclera, cornea, iris, ciliary body, vitreous, choroid, retina and macula act as a precursor for the cause of severe vision impairment and blindness. Most specifically the invention details sulfonic polymers and its formulation methods to target and control the activation loop of complement system at C3 level that controls over 80% complement activation and inflammatory damage. The underlying molecular targets are Factor B, Factor D, Factor H, Classical complement proteins or lectin based proteins such as Clq.

7 Claims, 13 Drawing Sheets

(56) References Cited

OTHER PUBLICATIONS

Morrison PW et al, Advances in ophthalmic drug delivery. Ther Deliv. Dec. 2014;5(12):1297-315, [on-line], [retrieved on Nov. 25, 2023]. Retrieved from the Internet <URL: https://www.future-science.com/doi/10.4155/tde.14.75> <doi: 10.4155/tde.14.75>.

Patel A et al, Ocular drug delivery systems: An overview. World J Pharmacol. 2013;2(2):47-64, [on-line], [retrieved on Nov. 25, 2023]. Retrieved from the Internet <URL: https://www.ncbi.nlm.nih.gov/pmc/articles/PMC4289909/> <doi: 10.5497/wjp.v2.i2.47>.

Peters K. Physiology and pathology of the C3 amplification cycle: A retrospective. Immunol Rev. Jan. 2023;313(1):217-224, [on-line], [retrieved on Nov. 25, 2023]. Retrieved from the Internet <URL: https://onlinelibrary.wiley.com/doi/full/10.1111/imr.13165> <doi: 10.1111/imr.13165>.

Xu H et al, Targeting the complement system for the management of retinal inflammatory and degenerative diseases. Eur J Pharmacol. Sep. 15, 2016;787:94-104, [on-line], [retrieved on Nov. 25, 2023]. Retrieved from the Internet <URL: https://www.ncbi.nlm.nih.gov/pmc/articles/PMC5026403/> <doi: 10.1016/j.ejphar.2016.03.001>.

Yadav MK et al, Molecular basis of anaphylatoxin binding, activation, and signaling bias at complement receptors. Cell. Oct. 26, 2023;186(22):4956-4973.e21, [on-line], [retrieved on Nov. 25, 2023]. Retrieved from the Internet <URL: https://pubmed.ncbi.nlm.nih.gov/37852260> <doi: 10.1016/j.cell.2023.09.020>.

Moreau JM et al, Abstract of "Effectiveness of ciprofloxacin-polystyrene sulfonate (PSS), ciprofloxacin and ofloxacin in a *Staphylococcus keratitis* model". Curr Eye Res. Aug. 1998;17(8):808-12, [on-line], [received on May 31, 2024]. Retrieved from the Internet <URL: https://pubmed.ncbi.nlm.nih.gov/9723996/> <https://doi.org/10.1080/02713689808951262>.

Murakami Y, et al, Interaction of poly(styrene sulfonic acid) with the alternative pathway of the serum complement system. J Biomater Sci Polym Ed. 2005;16(3):381-95 [on-line], [received on May 31, 2024]. Retrieved from the Internet <URL: doi: 10.1163/1568562053654095>.

Gertsman BB et al, Use of sodium polystyrene sulfonate in sorbitol in the United States, 1985-1989. Am J Kidney Dis. Nov. 1991;18(5):619-20 [on-line], [received May 31, 2024]. Retrieved from the Internet <URL: doi: 10.1016/s0272-6386(12)80663-9> <https://pubmed.ncbi.nlm.nih.gov/1951347/>.

Setoyama H et al, The potential of anticomplement synthetic sulfonic polymers for xenotransplantation. Transplant Proc. Feb. 1998;30(1):67-70 [on-line], [received May 31, 2024]. Retrieved from the Internet <URL: doi: 10.1016/s0041-1345(97)01181-0> <https://pubmed.ncbi.nlm.nih.gov/9474959/>.

Inaba S et al, Potassium-adsorption filter for RBC transfusion: a phase III clinical trial. Transfusion. Dec. 2000;40(12):1469-74 [on-line], [retreived May 31, 2024]. Retrieved from the Internet <URL: doi: 10.1046/j.1537-2995.2000.40121469.x> <https://pubmed.ncbi.nlm.nih.gov/11134566/>.

Office of the Federal Register, National Archives and Records Administration. Federal Register vol. 37, No. 158, Aug. 15, 1972. Government. Office of the Federal Register, National Archives and Records Administration [on-line], [retrieved on Dec. 23, 2023]. Retrieved from the Internet <URL: https://www.govinfo.gov/app/details/FR-1972-08-15>.

* cited by examiner

| Year | Blindness (millions) | Severe Vision Impairement (millions) | Global number Affected (millions) |
|---|---|---|---|
| 1990 | 31 | 160 | 191 |
| 2010 | 34 | 199 | 233 |
| 2030 | 55 | 330 | 385 |
| 2050 | 115 | 588 | 703 |

FIG. 1

| S. No. | Proteins of Complement Activation Loop | Sulfonic Nanopolymer Complement proteinbinding % (Dose: 60 mg) | PSCH2OH-SO3, Complement proteinbinding % (Dose equivalent to 60mg of Sulfonic Nano polymer |
|---|---|---|---|
| 1. | C3 | 0 | 0 |
| 2. | Factor B | 37 | 14 |
| 3. | Factor D | 100 | 93 |
| 4. | Factor H | 100 | 0 |
| 5. | Factor I | 0 | 0 |

FIG. 3

Sulfonic Nanopolymer : Islet Cell Transplant Data: ETBOND TECHNOLOGY

| Donor | Recipient | No. of islet cells implanted | Sulfonic Nanopolymer (<100 nm) | Graft Survival (Mean) | Variation (SD) | Comments |
|---|---|---|---|---|---|---|
| Hamster | Mouse<br>(STZ DM) | 1000<br>1000<br>1000 | | 7.0<br>31.5<br>77.4 | 3.5<br>42.4<br>21.7 | --- Control |
| Hamster | NOD<br>Mouse<br>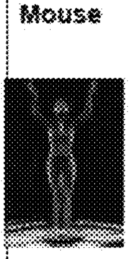 | A 1000<br>B 1000<br>C 1000 | | 6.0<br>10.2<br>84.6 | 0<br>2.0<br>27.8 | As opposed to control of 6 days our drug induce islet cell tolerance for 84.6 days. |
| Rat | Mouse<br>(STZDM) | 500 | 78.6 | | 35.7 | |

FIG. 4

ETBOND TECHNOLOGY: RESEARCH AND DEVELOPMENT

| US PHYSICIANS | 1 M BY 2023 PHYSICIANS AWARENESS |
|---|---|
| USERS OF SPS | 1 M Physiciaans have used this medicine at 60 gram orally per day to lower potassium in intensive care units during their resident training |
| KEY ADVANCES IN GENOMICS | 1Kumar Shah |
| KEY ADVANCE IN FUNDAMENTALS OF IMMUNOLOGY | 1As above |
| HEMODIALYSIS REVOLUTION POLYSULFONE | 1As above |
| FACTOR H/D MODULATION | 1 As above |
| CURE OF DIABETES NOD MICE | 1 As above |
| APPLICATIONS | |
| A. ANTHRAX | 1 As above |
| B BLINDNESS | 1 As above |
| C. CANCER | 1 As above |
| D. DIABETES COMPLICATIONS | 1 As above |
| E. PREGNANCY | 1 As above |
| F. BLOOD DISORDERS | 1 As above |
| G. KIDNEY DISEASES | 1 As above |
| H. PANDEMICS: COVID-19 | 1 As above |

Human safety improvement: >1000 times at <600 mg/day from 60 gram dose

A. POWER OF OBSERVATION 1 IN MILLION / disease x 20 diseases
B. POWER OF DATA DOCUMENTATION: OVER 16,400 PUBLICATIONS "https://www.ncbi.nlm.nih.gov/pmc/?term=FACTOR+H"
C. POWER OF HUMAN SAFETY: >1000 times safety at <600 mg/day from 60 gram approved dose
D. ADVANCING FROM BENCH TO BEDSIDE WITH "ZERO TOLERANCE TO TIME"
E. FINANCIAL ENGINEERING: COST: REDUCE FROM 1 BILLION TO 1 DOLLAR. Note currently approved complement inhibitor Ecluzumab cost >100000.00/year
F. TIME ENGINEERING: 10 YEARS OF DEVELOPMENT TIME TO LESS THAN 1 MONTH FRO "Right TO TRY Approval"

FIG. 6

Table 1. Complement-based therapeutic targets and their potential applications in organ transplantation.

| Molecular mediators | Mechanism of action | Experimental/clinical studies |
|---|---|---|
| Eculizumab | C5, abrogate terminal complement activation | Human (ClinicalTrials.gov Identifiers, NCT02013037, NCT01327573, NCT02113891) |
| C1-INH (Berinert) (CINRYZE) | Prevent complement initiation via the classical and lectin pathways | Human (ClinicalTrials.gov Identifiers: NCT02134314, NCT01134510, NCT01035593, NCT01147302) |
| TP-10 (sCR1) | Inactivate C3a and C5a convertases | Human (a randomized, placebo-controlled trial in lung transplantation) |
| CR2-FH | Inhibits alternative complement pathway | Mice (heart transplants) |
| CR2-Crry | Inhibits all complement pathways | Mice (heart and trachea transplants) |
| NOX-D19, NOX-D20, NOX-D21 | Specifically inhibits complement component C5a | Mice (trachea transplants) |
| Y-CVF | A C3 inhibitor | Non-human primates |

FIG. 11

PROPHYLAXIS AND THERAPY FOR OCULAR DISEASES LEADING TO BLINDNESS

BACKGROUND OF THE INVENTION

1. Field of the Invention

Major advances in eye diseases have occurred. The field of complement mediated eye diseases: its breadth, depth and urgency to solve this problem of "Complement based hyper inflammation" as a potential prophylactic and therapeutic measures to prevent possible blindness is under appreciated and remains unmet medical needs.

2. The Prior Art

The urgency for the need to target complement mediated hyper inflammation to solve the growing global problem of severe vision impairment and blindness is reflected in following statistics.

Vision loss Expert Group studied statistics from 1990 to 2050. They estimate the current status of moderate to severe vision impairment and blindness and projected cases in future as shown in FIG. 1.

According to United Nations Data: Global population was 7.8 Billion by 2020 and will rise to 9.7 billion by 2050. The aging population in 2015, there where 901 million people over the age of 60 (12%) of global population. By 2050, the number of people over the age of 60 is predicted to increase to 2.1 billion or (22%). Above age 80 population in 2015 was 125 M. This will increase three folds by 2050 to 434 M.

Prevalence of Vision impairment rapidly increase with age. By age 60 1 in 9 people either have blindness severe vision impairment. By age 80 one in 3 people will have blindness or will have severe vision impairment. The severity of the problem is discussed in Ackland P., "World blindness and visual impairment: despite many successes, the problem is growing" published in Community Health Journal, Vol. 30, Number 100, 2017, the entire contents of which are incorporated herein by reference thereto.

The Role of Complement System in Eye Diseases: Complement system, as explained in this educational video link https://www.youtube.com/watch?v=BSypUV6QUNw have following key elements of complexity.

Other research on the relationship between the complement system and ocular diseases is presented by Xu H. and Chen M., "Targeting the complement system for the management of retinal inflammatory and degenerative diseases," available at ncbi.nlm.nih.gov/pmc/articles/PMC5026403/?report=reader, the entire contents of which are incorporated herein by reference thereto.

Complement system evolved over 700 million years ago and is an army of over 30 different proteins that work together in a complex and elegant dance to stop intruders.

All in all, about 15 quintillion complement proteins are saturating every fluid in our body. A healthy adult has about 5.3 micro molar of C3 in their blood. For this calculation, round it to 5. One micro molar equals 6.022×10^17 molecules in a liter. An average adult contains roughly 5 liters of blood. So 6×10^17×5×5=1.5×10^19, or 15 quintillion One of the key players of our immune system is the complement system. An army of millions and trillions of tiny bombs, which work together in a complex and elegant dance to stop intruders in your body.

Dysfunction of complement system will lead to explosion of tiny bombs damaging host tissues. In eyes it will lead to damage to ocular tissues. In ocular tissues this can contribute to moderate to severe vision impairment and blindness.

Examples of such eye diseases where complement mediated hyper inflammation can be potentially prevented and can be treated for blindness are diseases of anterior and posterior segments of eyes such as corneal injury, autoimmune uveitis (affecting choroid, iris and ciliary body), glaucoma, diabetic retinopathy and age related macular degeneration (AMD).

Certain diseases and injuries to the cornea may require corneal transplants as discussed in Armitage W. J. et al in "High-risk Corneal Transplantation: Recent Developments and Future Possibilities" published in Transplantation, December 2019, Volume 103, Number 12, the entire contents of which are incorporated herein by reference thereto. The researchers report "Furthermore, while partial-thickness (lamellar) keratoplasty has now become the preferred transplant procedure for many corneal disorders, full-thickness allograft remains the most frequently utilized treatment worldwide for corneal conditions associated with significant stromal opacity or vascularization such as bacterial, fungal, or viral infections; sever atopic disorders; ocular trauma and prior graft loss. Corneal opacity is reported to be between the second and fourth most common cause of blindness globally, but its prevalence in different geographical regions is poorly understood and probably underestimated. In India alone, the number of individuals with unilateral corneal blindness is projected to increase to >10 million by 2020. In contrast to other causes of blindness, a relatively high proportion of those affected are young, with approximately 20% of childhood blindness attributed to corneal disorders. Bilateral corneal disease resulting in total loss of vision is especially common in the developing world. Thus the potential societal impact of global progress in preventing corneal disease and restoring sight for individuals suffering from corneal blindness is substantial."

Below we briefly outline how complement mediated inflammation can contribute to vision loss and highlight the importance of "Complement Activation loop".

Several reports in the literature have suggested the presence of functionally active classical and alternative complement pathways in the cornea, aqueous humor, tears and retina. Various proteins which regulate the activation of the complement system, such as C1 inhibitor, DAF, MCP, CD59, factor I and factor H, have been reported to be present also in various ocular tissues, tears, aqueous and vitreous humor.

The relationship between Factor H, Factor I and C3 activation is described in Peters, K "Physiology and pathology of the C3 amplification cycle: A retrospective" published by Immunology Reviews, 2023; 313:217-224, the entire contents of which are incorporated herein by reference thereto. The research further explores the effects of complement with respect to AMD. Peters reports that, "Early studies of C3 metabolism showed that there was indeed a very high turnover of C3, which has a half-life of around 3 days, with similar values for other components of the system. But such a system needs physiological control to prevent excessive and potentially harmful generation of inflammatory complement molecules. At a meeting in Bruges when Chester Alper presented the now famous Boston patient, TJ, who suffered from recurrent bacterial infection, abnormalities of complement function, and profound reduction of C3, Lachmann suggested TJ be tested for what was then termed KAF (conglutinogen activating factor, now known as Factor I). Lachmann went on to show that TJ was totally deficient in Factor I (FI), and was able to reproduce the same complement profile in vitro by immunochemical depletion of FI. He further showed that purified FI restored TJ's complement function in vitro and in vivo. Many years later Lachmann et al. showed that an antibody which specifically reacted with C3b but not C3, inhibited binding of C3b to Factor B (FB), and prevented the complement activation induced by immunochemical FI depletion in vitro."

Complement system is continuously active at a low level in the normal rodent eye, but eye is protected from complement activation due to the presence of intra ocular complement regulators. This is present both in the intra ocular fluid as well as on the cell membrane such as corneal surface. This tightly regulates this spontaneous complement activation. Control of complement activation at the level of C3 convertase was sufficient to prevent complement-mediated intra ocular inflammation.

The contribution of complement mediated inflammation of eyes is detailed in the review articles by Jha P. Bora P. S. And Bora N S. In "The Complement system and Ocular Diseases" published in Mol Immunol 2007 September 44 (16): 3901-3908, the entire contents of which are incorporated herein by reference thereto. The article details how complement contribute to intra ocular inflammation in autoimmune uveitis and play an important role in corneal inflammation, age-related macular degeneration and diabetic retinopathy.

Clark S j and Bishop P. N. "The eye as a complement dysregulation hot spot" published in Semin Immunopathol 40:65-74; 2018 (DOI 10,1007/s00281-017-0649-6), the entire contents of which are incorporated herein by reference thereto. The article details how over activation of the complement cascade contribute to disease progression of glaucoma, diabetic retinopathy, and Age Related Macular Degeneration (AMD). The article takes in to consideration of unique anatomy of eye and gives careful emphasis on the breadth and depth of complement mediated inflammation and how it should be targeted through novel formulation methods.

Both articles detail evidences derived from both animal models and patient studies to support the concept that complement inhibition is a relevant therapeutic target in the treatment of various ocular diseases. Currently, several clinical trials using complement inhibitors are going on. It is possible that, in the near future, complement inhibitors might be used as a therapeutic agents in eye clinics.

Dreismann A. K. and Halam T. M. et. a. Review article. "Gene targeting as a therapeutic avenue in diseases mediated by the complement alternative pathway" published in Immunological Reviews: 2023; 313; 402-419, the entire contents of which are incorporated herein by reference thereto. The paper reviewed gene targeting of alternate pathway-mediated complement inflammation for example in eye disease such as Age related macular degeneration. The gene targeting includes RNA targeting via RNA interference (RNAI) or antisense oligonucleotides (ASO), DNA targeting using clustered regulatory interspaced short palindromic repeats (CRISPER) technology, and gene targeting via Adeno associated virus vectors (AAV).

Harrison R. A., Harris C. L. and Thurman J. M. reviewed "The complement alternative pathway in health and disease-activation or amplification?" published in Immunological Reviews: 2023; 313; 6-14, the entire contents of which are incorporated herein by reference thereto. They report on the alternative pathway (AP) or amplification loop (AL) of C3 activation as, "[M] ore subtle functional defects in AP/AL regulation contribute to common diseases, including age-related macular degeneration. As described by de Jong et al genetic variants in complement genes account for more than 50% of the risk of age-related macular degeneration, a major cause of vision loss. This has led to development of AP/AL-related biomarkers of AMD risk, and in several clinical trials of complement inhibitory drugs." In discussing Factor H (FH) they note, "The interaction of FH with C3b and/or polyanionic surfaces is complicated by the more recently discovered Factor H-related (FHRs) proteins. FHRs compete with FH in binding both to C3b and to surfaces that have been termed FH-deregulators. As such they too can act as positive regulators of AP/AL."

Gibson B. G., Cox T. E. and Marchbank K. J. reviewed "Contribution of animal models to mechanistic understanding of Alternative Pathway and Amplification Loop (AP/AL)-driven Complement-mediated Diseases" published in Immunological Reviews: 2023; 313; 194-216, the entire contents of which are incorporated herein by reference thereto. They report, "In summary, soluble complement regulatory FH and its role in controlling AP/AL is critical to the development of complement mediated kidney disease in humans, pigs and mice. Furthermore, FH is crucial for the regulation of complement activation on the extracellular matrix . . . . In the absence of FH, spontaneous activation of the AP occurs leading to complete consumption of C3 and FB, and in this manner FH deficiency is highly analogous to use of CVf to actively deplete complement." As illustrated in the article (shown in FIG. 5) and described, "The AP/AL is highly conserved between mouse and human, enabling human proteins (green boxes) to be used and function adequately within the murin system, for example, human Factor H (FH) easily regulates C3. Conversely, human C3 is not regulated by murin FH (or Crry) but can be activated and binds to mouse Factor B (FB) and Factor D (FD) (red boxes)."

This invention details the application of first principle to accelerate prophylaxis and therapy of blindness.

A first principle is a basic assumption that cannot be deduced any further. Over two thousand years ago, Aristotle defined a first principle as "the first basis from which a thing is known."

First principles thinking is a fancy way of saying "think like a scientist." Scientists don't assume anything.

First principles thinking (also called reasoning from first principles) requires breaking down a problem into its fundamental building blocks, its essential elements, asking powerful questions, getting down to the basic truth, separating facts from assumptions and then constructing a view from the grounds up.

First principle or 'knowledge-based' models start from the basis of established science that are generally accepted and have been extensively verified.

This is applied to the study of complement system in the context of "Recent advances in genomics and fundamentals of immunology". This has helped us to simplify the working of the system to key element that is Amplification loop of Complement system that control 80% of complement activation.

Identifying downstream effects of such complement activation that contribute to eye tissue damage. This refers to C3a-C5a activations causing liberation of anaphylotoxins and its down steam interactions with C3aR and C5a R (R means Receptors) to stimulate inflammatory cytokines. Additional research on this is provided by Yadav M. K. et al, "Molecular basis of anaphylatoxin binding, activation, and signaling bias at complement receptors," 2023, Cell 186. 4956-4973, the entire contents of which are incorporated herein by reference thereto.

Developing the drug and formulation methods for blocking amplification ion loop of complement system requires three basic steps.

Obtaining pre-clinical proof of concept data

Developing human safety data

Identifying most efficient regulatory pathway for quick clinical implementation of technology advances.

Above requires extensive literature review of "Recent Advances in the Fundamentals of Immunology and how it can be applied in eye diseases.

Further, it also involved studying of the competitive molecular targeting of complement system as drug development process by biopharmaceutical industry and identifying key regulatory obstacles in drug development.

Immunity is a major barrier in the translational development of biopharmaceutical drugs. The human safety issue remains a problem that affects companies in both clinical trials and in post marketing phase. The drug industry's problems associated with meeting the regulatory safety and efficacy standards for new products are analyzed in an FDA report on innovation stagnation published in 2004 (FDA). The cost of successful product from bench to bed-side has soared to US $1.7 billion by 2002. The US Food and Drug Administration estimates a cost saving of US $100 Million if the human safety of new drugs could be predicted with 10% accuracy.

SUMMARY OF THE INVENTION

It is the first object of the invention to identify molecular targets involved in "Complement activation Loop at C3 level"

It is second object of the invention to develop a drug and demonstrate proof of concept data by in-vitro studies in the laboratory setting. This is done by molecular targeting and kinetic study of such molecular targets of proteins of "C3 amplification ion loop"

It is the third object of the invention to develop a proof of concept data by in-vivo studies in animal models to show "C3 complement activation loop can be inhibited and it will have therapeutic anti-inflammatory effects.

It is the fourth object of the invention to define the clinical safety of the drug at human level.

It is the fifth object of the invention to find the most efficient regulatory path "Right to Try" to meet the growing unmet medical needs for prophylaxis and therapy of blindness.

These and other related objects are achieved according to an embodiment of the invention directed to a method for prophylaxis and therapy for complement-mediated hyper-inflammatory ocular diseases. Initially, a polystyrene sulfonate based pharmacological composition is formulated. The polystyrene sulfonated based pharmacological composition is one of sodium polystyrene sulfonate, calcium polystyrene sulfonate, formulation variations thereof, or combinations thereof. A patient is selected from one suffering from a complement-mediated hyper-inflammatory ocular disease. The pharmacological composition is administered to the patient, wherein the pharmacological composition selectively targets key proteins involved in the C3 amplification loop to provide prophylaxis and therapy for the complement-mediated hyper-inflammatory ocular disease.

The complement-mediated hyper-inflammatory ocular diseases are defined as diseases that may occur on the surface of the eye such as the sclera, cornea, tear fluid or anterior segment such as iris, choroid, ciliary body or aqueous humor or posterior segments of the eye such as vitreous humor or retina.

The complement-mediated hyper-inflammatory diseases may occur due to trauma, surgery, implant of lens, transplant of cornea or its complications, laser therapy of retina or in diseases of eyes such as Diabetic retinopathy, retinitis pigmentosa and age related macular degeneration (AMD).

The term prophylaxis use of the drug includes earliest use to prevent the occurrence of complement mediated hyper inflammation. Wherein therapeutic use includes earliest use of the drug to prevent progression of the complement mediated hyper inflammation and its progression of the disease to blindness.

The formulating step includes formulating a polystyrene sulfonate based pharmacological composition selected from the group consisting of fractional purified sodium polystyrene sulfonate, fractional purified calcium polystyrene sulfonate, or their nano polymer or its combinations thereof.

The pharmacological composition selectively targets key proteins involved in the C3 amplification loop, wherein the key proteins are selected from the group consisting of Factor B, Factor D, Factor H, or its amplifying proteins of classical based systems, proteins of lectin based systems, or combinations thereof.

The pharmacological composition is administered in appropriate dosage either locally as eye drop, emulsion or gel formulation or systemically either in the injection form as intramuscular, intravenous or oral route and may include combinations with current and evolving ocular drugs.

The complement-mediated hyper-inflammatory ocular diseases are degenerative diseases that lead to blindness. The complement-mediated hyper-inflammatory ocular diseases are diseases of the anterior or posterior segments of the eye. The complement-mediated hyper-inflammatory ocular diseases are diseases of sclera, aqueous humor, vitreous humor, choroid or retina. The complement-mediated hyper-inflammatory ocular diseases are corneal injury, autoimmune uveitis, glaucoma, diabetic retinopathy or age related macular degeneration. The complement-mediated hyper-inflammatory ocular diseases is autoimmune uveitis affecting a choroid, autoimmune uveitis affecting an iris, or autoimmune uveitis affecting a ciliary body. The complement-mediated hyper-inflammatory ocular diseases is age related macular degeneration.

The formulating step includes formulating a polystyrene sulfonate based pharmacological composition selected from the group consisting of fractional purified sodium polystyrene sulfonate, fractional purified calcium polystyrene sulfonate, or combinations thereof. Alternatively, the formulating step includes formulating a polystyrene sulfonate based pharmacological composition selected from the group consisting of sodium polystyrene sulfonated nanopolymer, calcium polystyrene sulfonated nanopolymer, or combinations thereof. Optionally, the formulating step includes formulating a polystyrene sulfonate based pharmacological composition selected from the group consisting of sodium polystyrene sulfonated nanopolymer, calcium polystyrene sulfonated nanopolymer, or combinations thereof. In another embodiment, the formulating step includes formulating a polystyrene sulfonate based pharmacological composition selected from the group consisting of fractional purified sodium polystyrene sulfonate, fractional purified calcium polystyrene sulfonate, or combinations thereof.

The pharmacological composition selectively targets key proteins involved in the C3 amplification loop, wherein the key proteins are selected from the group consisting of Factor B, Factor D, Factor H, proteins of classical based systems, proteins of lectin based systems, or combinations thereof. The pharmacological composition is administered in combination with ocular drugs. For example, the pharmacological composition is administered with ciprofloxacin, ofloxacin or combinations thereof.

The administering step includes administering the pharmacological composition to the patient intravenously in a dose of 5-10 mg/kg body weight in 250 ml-500 ml 0.85% saline. Alternatively, the administering step includes administering the pharmacological composition to the patient orally in a dose of 5-10 mg/kg body weight with a pharmaceutically acceptable excipient. In another option, the administering step includes administering the pharmacological composition to the patient topically. The pharmacological composition may be incorporated in a liquid, gel, or ointment carrier.

BRIEF DESCRIPTION OF THE DRAWINGS

These and other aspects, features and advantages of present invention will be described or become apparent from the following detailed description of the preferred embodiments, which is to be read in connections with the accompanying drawings.

FIG. 1 is a table presenting Vision loss Expert Group studied statistics from 1990 to 2050. They estimate the current status of moderate to severe vision impairment and blindness and projected cases in future.

FIG. 3 is a Table which shows Binding characteristics of complement proteins with polystyrene sulfonated.

FIG. 4 is a Table presenting In-vivo Mice efficacy data.

FIG. 6 is a summary of our research and development methodology.

FIG. 11 is a table showing complement-based therapeutic targets.

DETAILED DESCRIPTION OF THE PREFERRED EMBODIMENTS

FIG. 1 is a table presenting Vision loss Expert Group studied statistics from 1990 to 2050. They estimate the current status of moderate to severe vision impairment and blindness and projected cases in future.

Figure 2:
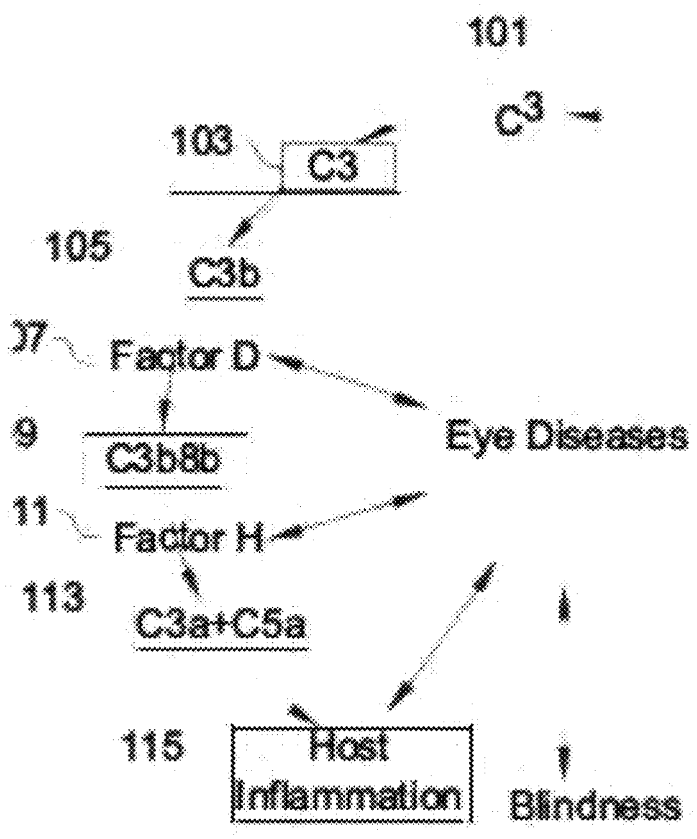
FIG. 2 explains the role of complement activation loop at C3 and how it contributes to eye diseases of anterior and posterior segments of the eye. This includes: corneal injury; Autoimmune uveitis (affecting iris, ciliary body); Diabetic retinopathy and age related macular degeneration (AMD).
Figure 5:
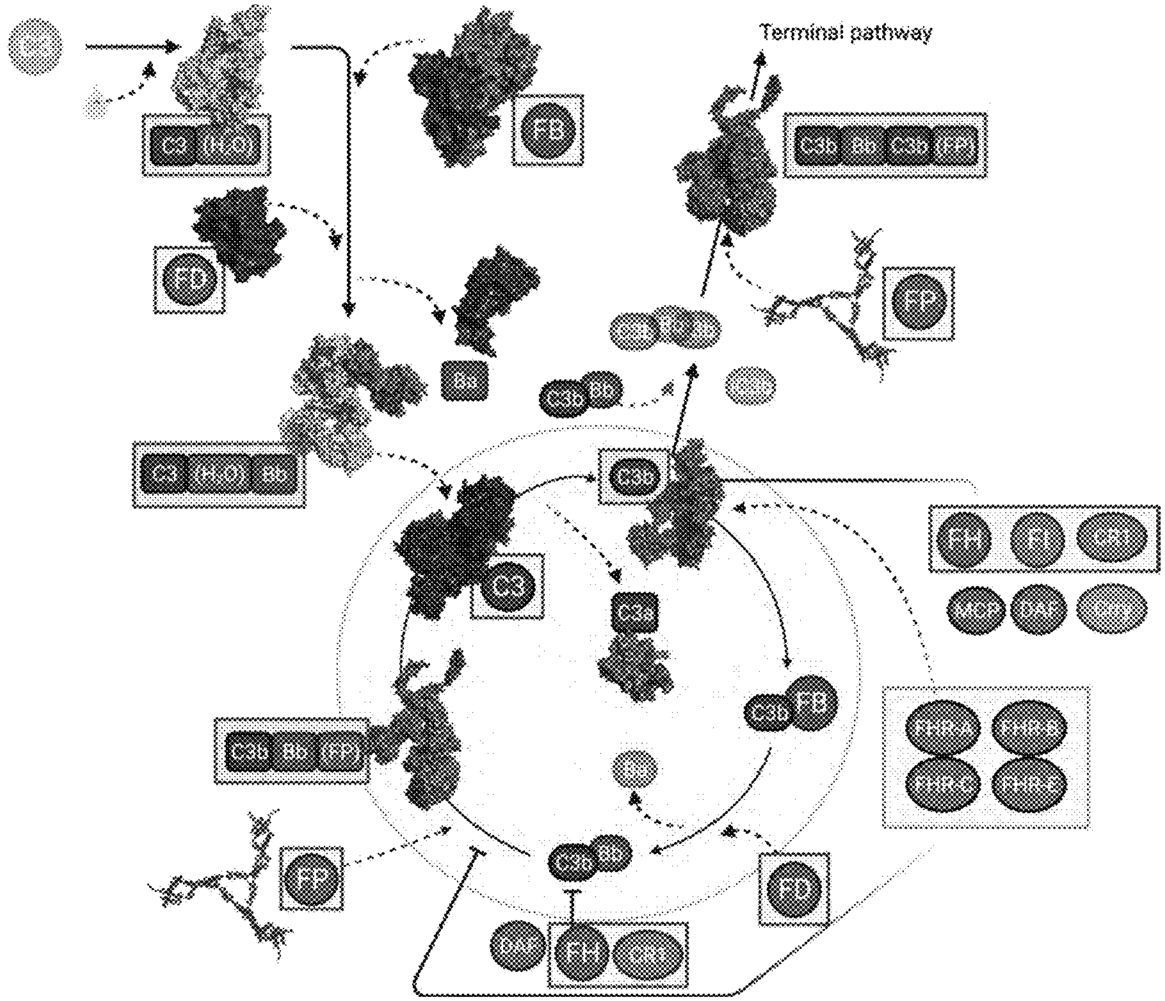
FIG. 5 is a diagram from the Gibson article illustrating how Factor H regulates C3.

FIG. 2 explains the role of complement activation loop at C3 and how it contributes to eye diseases of anterior and posterior segments of the eye. This includes: corneal injury; Autoimmune uveitis (affecting iris, ciliary body); Diabetic retinopathy and age related macular degeneration (AMD).

Figure 7:
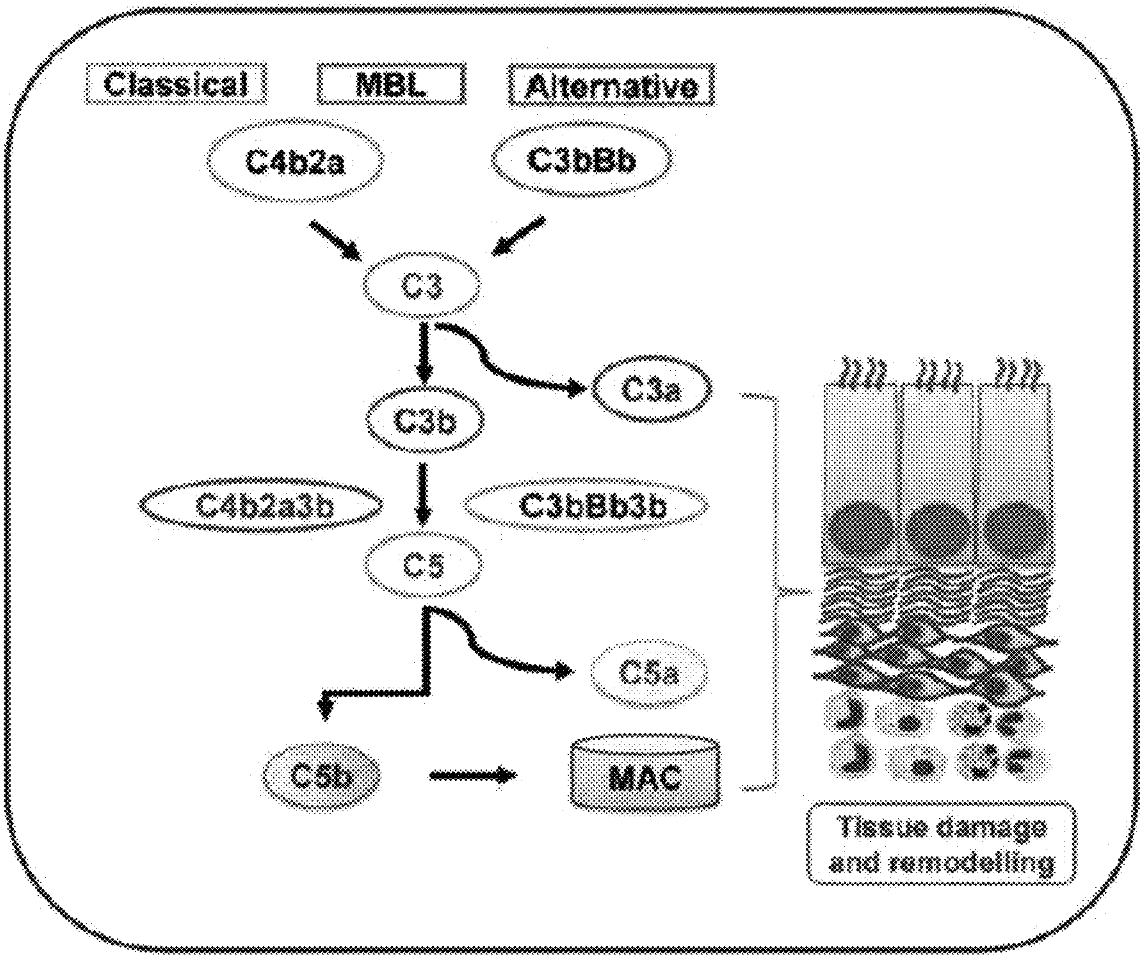
FIGS. 7-10 are a series of diagrams illustrating various proteins and their interaction within the immune system.
Figure 8:
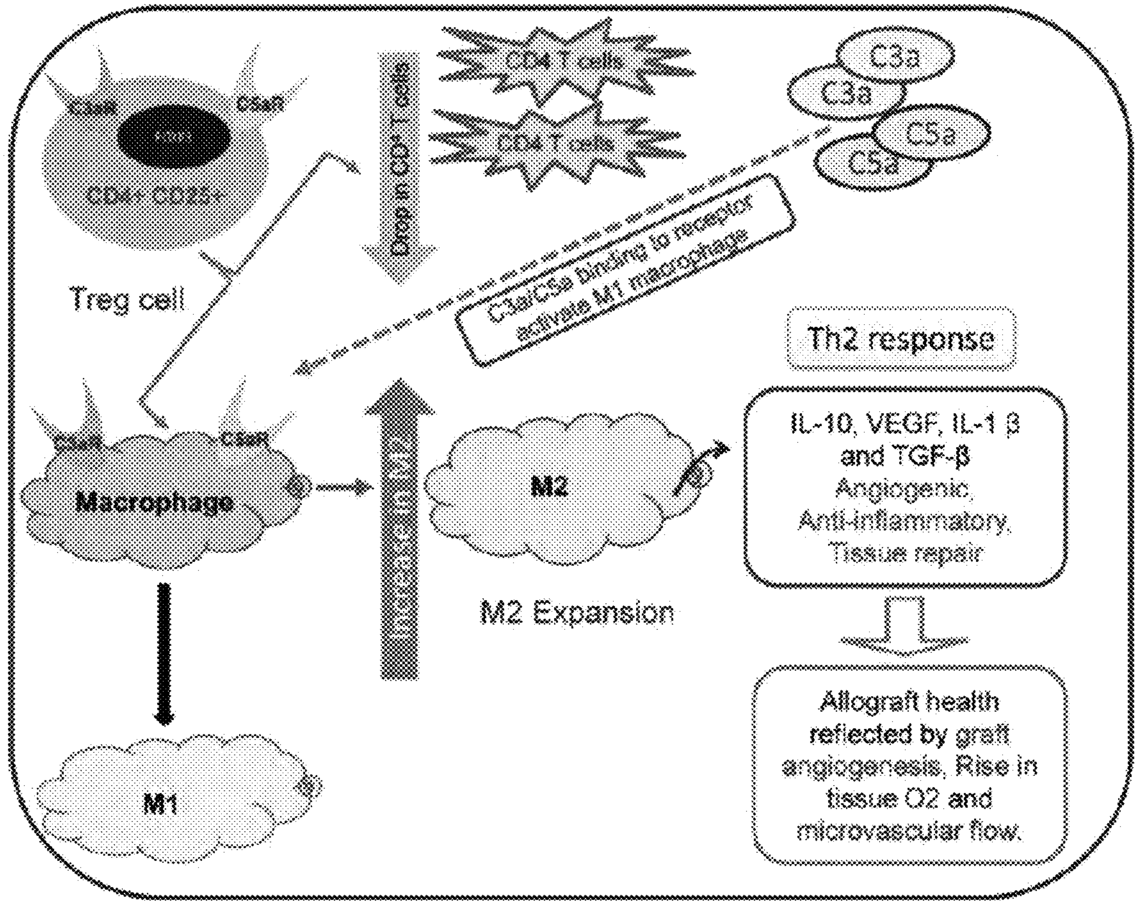
Figure 9:
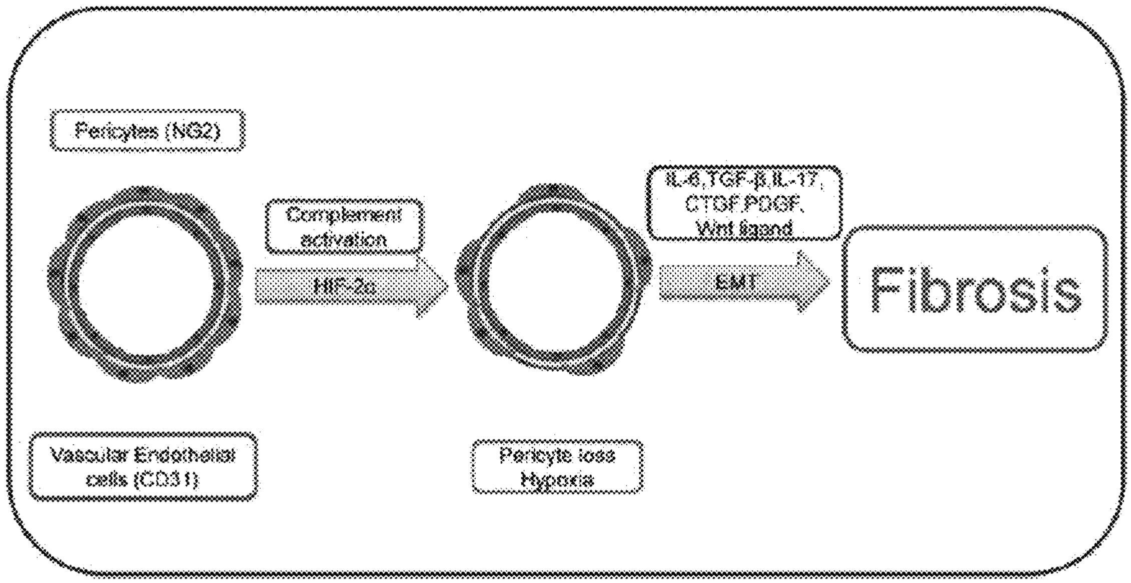
Figure 10:
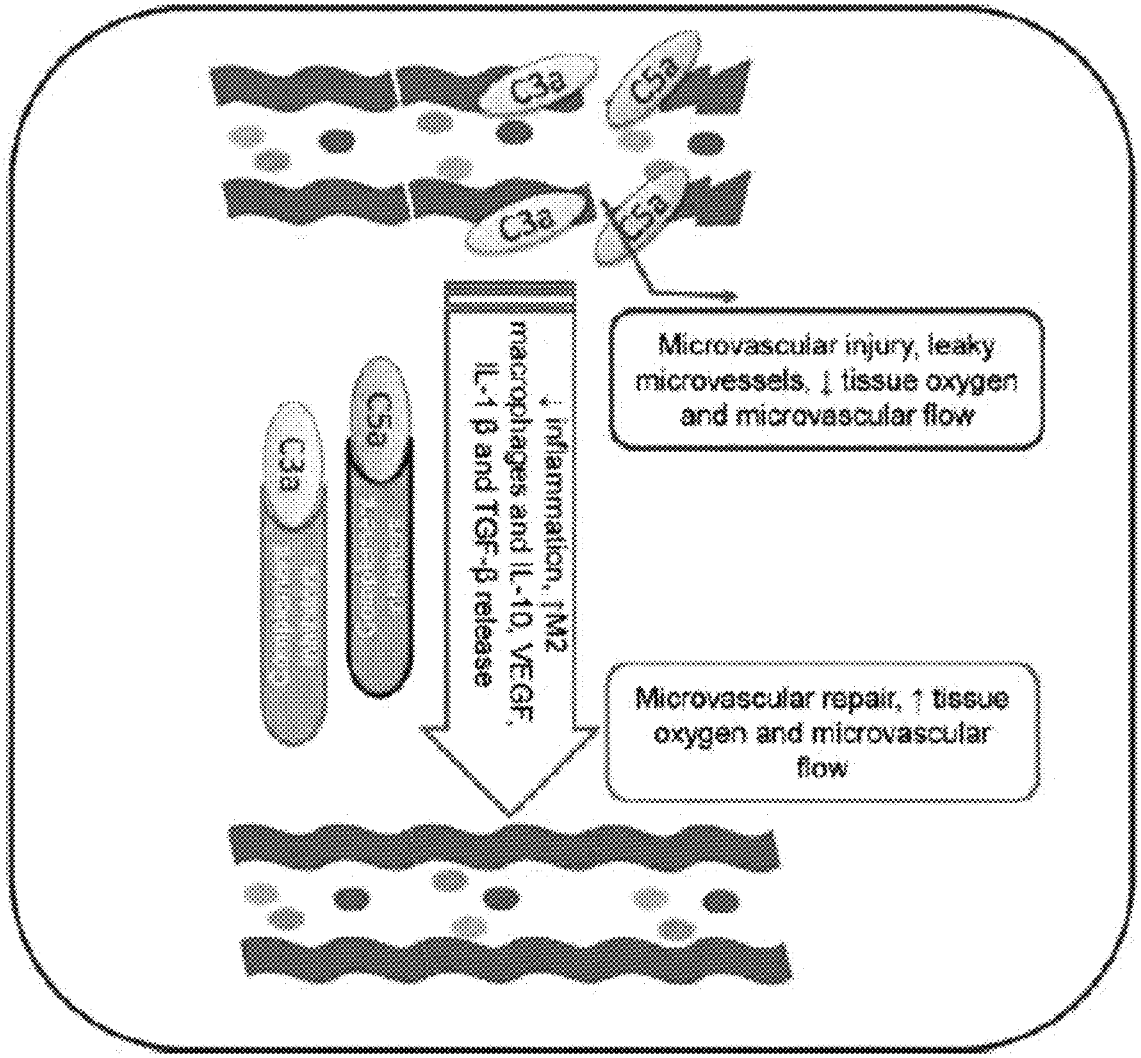

C3 (101) represents three activating pathways (e.g. Classical, Lectin and Alternate complement system, see FIG. 7).

C3 (103) is the common end product of C3 that is C3b (105). This is an activated C3 with thioester bond removed.

Factor D (107) is a serine protease activating protein of alternate complement system, C3bBb (109) is a C3 Convertase.

Factor H (111) is a complement regulatory protein that has been assigned a new role of recognizing self, as per recent advances in genomics and fundamentals of immunology playing a dominant role over other immune regulatory molecules present on host cell surface.

Factor H is mutated in AMD, in diabetic retinopathy, the cell surface glycosylation is abnormal and in corneal injuries there is damage to immune regulatory molecules including Factor H. These factors hyper activate "C3 Amplification loop" generating more and more C3bBb (109).

C3a-C5a (115) is anaphylotoxin and breakdown product of C3bBb (109) that reacts with receptors of C3a and C5a (Not shown) to stimulate production of inflammatory cytokines. They contribute to eye inflammation and eventually leads to blindness.

FIG. 2 shows the Application of Recent Advances in Genomics and Immunology for Prophylaxis and therapy of Blindness These above objectives are met as follows:

Endocrine Technology, LLC is NY based Biotechnology Company established on Feb. 12, 2002. The organization is a physician based biotechnology company—that actively treats large numbers of patients with diabetes and its complications.

Initial efforts were directed for the cure of Type 1 Diabetes in early 1990s. While working at a largest transplant center in Asia for "Kidney diseases" in Ahmedabad, G. S., India, we have noticed that the success of hemodialysis in the treatment of "chronic Renal Failure" was due to major improvements in "hollow fibers used for Hemodialysis." This prevented the occurrence of life threatening "acute respiratory failure" which was common place earlier.

We capitalized on these advances to develop technology to target "Amplification of complement loop at C3 level"

We present preclinical proof of concept data to modulate "Amplification of complement loop at C3 level" by molecular targeting of Factor D, Factor H and Factor B. These are the key components involved in C3 mediated amplification loop of complement system. Classical and left mediated activation is also amplified by C3 amplification loop.

Identification of Key Molecular Targets: A careful perusal of Recent Advances in Complement System suggest that Alternate Complement System is the key driver of Immune pathogenesis of Ocular diseases where there is proximal complement system activation.

Factor D is a 25 kD fluid protein of Alternate Complement System. It is a key driver of proximal complement activation. The relentlessly activated proximal complement system cause down stream activation of inflammatory mediators that is key driver of ocular inflammation Factor H is a complement regulatory protein that has been assigned a new role of recognizing self, as per recent advances in genomics and fundamentals of immunology playing a dominant role over other immune regulatory molecules present on host cell surface.

Factor H is mutated in AMD, in diabetic retinopathy, the cell surface glycosylation is abnormal and in corneal injuries there is damage to immune regulatory molecules including Factor H. These factors hyper activate "C3 Amplification loop" generating more and more C3bBb. C3a-C5a is anaphylotoxin and its breakdown product of C3bBb that reacts with receptors of C3a and C5a to stimulate production of inflammatory cytokines. They contribute to eye inflammation and eventually leads to blindness.

The binding of Complement amplification loop proteins at C3 level was studied for Factor B. Factor D, Factor H as well as for Factor I proteins. The studies involved binding kinetics of sulfonic nanopolymer and other polymers. NHS with buffer was used as normal control. The dose of polymers used was standardized.

The NHS in (1:4) dilution with each of above polymers was incubated at 37*C in the water bath with gentle agitation for half hours to 1 hour durations in a series of experiments. The binding activity of complement proteins in the serum was analyzed in duplicate and mean result is depicted. The key results are presented in FIG. 3 which shows Binding characteristics of complement proteins with polystyrene sulfonated.

The Assay incubation time was 60 min at 37*C, sulfonic nano polymer used was (60 mg=1056 cm2) and PSCH2OH—SO3 130 mg=1092 cm 2. The complement protein concentrations were measured in the supernatant and the specific adsorption was determined from the loss of protein observed in the presence of polymers as compared to control incubation.

In-Vitro Data: A. The drug application is based on the fact that as shown above it is a complement inhibitor of Factor D that will inhibit C3a-5a mediated anaphylotxon responses and also inflammatory responses due to its subsequent interactions with C3a and C5a receptor proteins on cell surfaces. Ocular inflammation is due to relentless activation of C5a and its interactions with C3aR and C5aR (receptors) liberating inflammatory cytokines.

In-vitro Data: B. The drug also inhibits Factor H. As shown above, Factor H is a dominant immune regulatory molecule of Alternate complement system that protect host in both at fluid and over cell membrane. This protein is mutated in age related macular degeneration (AMD) causing complement activation. In diabetic retinopathy, abnormal glycosylation on host cell surface contributes to complement activation. In Corneal injuries the, immune regulatory barrier is broken down leading to complement hyper activation.

In-vivo mice data: It inhibits the Complement system when the drug is given intravenously at 0.5 mg/kg body weight leading to inhibition of CH50 activity.

In-vivo Mice efficacy data: It has ben used successfully to inhibit inflammation in small animal models including Non Obese Diabetes (N.O.D.) Mice for the cure of diabetes as shown in FIG. 4.

Details Of Polystyrene Sulfonate

HISTORY: PSS is an endocrine drug originally introduced to medicine in 1935 and was formally approved in the USA in 1975. It has been used since 1975 for the therapy of high potassium. (Gerstman B. B. and Platt R. Uses of sodium polystyrene sulfonate in sorbitol in the United States, 1985-89. A J. of Kidney Dis., 1991:15, No. 5, 619-620; Sodium polystyrene sulfonate, Martindale: The complete Drug Reference, 32nd edition, edited by Parfitt K., Pharmaceutical Press, 1999:995-996). Its ability to manipulate immune system, provide antibacterial and antitoxin effects have overlapping basic principles defined in endocrinology and immunology. Ideas and observations from clinics can be brought to the laboratory or to a more basic level of translational research hierarchy for further investigation as shown by the new applications of an established drug.

PSS is a globally available drug at cost effective prices. (Sodium polystyrene sulfonate, Martindale: The complete Drug Reference, 32nd edition, edited by Parfitt K., Pharmaceutical Press, 1999:995-996). The mean approved dosage for the therapy of established indications, such as the therapy of high potassium, is 90 grams per day.

Based on the immune modulation data reported in-vitro and in-vivo, the dose required appears to be less than a gram per day. The drug is preferably given in the dose of 5-10 mg/kg body weight. It is given as intravenous infusion in 250 ml-500 ml 0.85% saline over 2-3 hours to permit action of this drug at tissue or blood level where it is needed most.

The frequency of doses could be once or twice a day. The mucosal safety data and blood contact safety data is readily available at this dosage. (Setoyama H., Inoue K., Iwata H. et al. The Potential of Anti-Complement Synthetic Sulfonic Polymers for Xenotransplantation. Transplantation Proceedings, 1998, 30:67-70; Gerstman B. B. and Platt R. Uses of sodium polystyrene sulfonate in sorbitol in the United States, 1985-89. A J. of Kidney Dis., 1991:15, No. 5, 619-620; Sodium polystyrene sulfonate, Martindale: The complete Drug Reference, 32nd edition, edited by Parfitt K., Pharmaceutical Press, 1999:995-996; Inaba S., Nibu K., Takano H. et al. Potassium adsorption filter for REC transfusion: A phase iii clinical trial. Transfusion, 2000; 40:1469-1474. The entire contents of which is incorporated herein by reference thereto.)

Thus, combining this drug with an anti-microbial, such as, for example, ciprofloxacinlin (Moreau J. M., Green L. C., Engel L. S. et al. "Effectiveness of ciprofloxacinlin-polystyrene sulfonate (PSS), ciprofloxacin and ofloxacin in a *Staphylococcus keratitis* model," Curr Eye Res, 1998, 17 (8): 808-12, the entire contents of which is incorporated herein by reference thereto), provides both anti-microbial and immune modulation therapy. The doses, frequency and duration are required to be determined based on outcome and monitoring of surrogate immune parameters related to the complement system and CD 4 counts, as well as routine parameters of infection. The oral dose may be added as desired based on clinical condition.

A variety methods to administer pharmaceutical compositions to treat ocular diseases is discussed in Morrison P. W. J and Khutoryanskiy V. V., "Advances in ophthalmic drug delivery," Ther. Deliv., 2014, 5 (12), 1297-1315, the entire contents of which are incorporated herein by reference thereto. These methods include ocular inserts, ocular implants, solubility enhancers, penetration enhancers, retention strategies, viscosity-enhancing polymers, in situ gelling systems, mucoadhesives, nanoparticles, contact lenses, drug-eluting intraocular lenses, intravitreal injection, intraocular implants and smart drug-delivery systems. The methods described in the report for ophthalmic drug delivery are incorporated herein by reference thereto.

Additional methods to administer pharmaceutical compositions to treat ocular diseases is presented in Patel A. et al, "Ocular drug delivery systems: An overview" appearing in World J Pharmacol, 2013; 2 (2): 47-64, the entire contents of which are incorporated herein by reference thereto. The novel systems described in the report are nanotechnology based ocular drug delivery, nanomicelles, nanoparticles, nanosuspensions, liposomes, dendrimers, in-situ gelling systems, contact lenses, implants and microneedles. The methods described in the report for ophthalmic drug delivery are incorporated herein by reference thereto.

Further scientific research on related materials is provided in Murakami Y. et al, "Interaction of poly (styrene sulfonic acid) with the alternative pathway of the serum complement system," Journal of Biomaterials Science, Polymer Edition, Vol. 16, 2005-Issue 3, the entire contents of which are incorporated herein by reference thereto. Additional research on ocular drugs following surgery is presented in Cao H., et al, "Risk Factors for Acute Endophthalmitis following Cataract Surgery: A Systematic Review and Meta-Analysis, Plos One, August 2013, Vol. 8, Issue 8, e71731, the entire contents of which are incorporated herein by reference thereto.

According to the FDA, a new formulation represents the unlabeled use of an established drug. FDA regulation permits the use of such drug by a licensed physician in life threatening infections. According to FDA commissioner Charles C. Edwards, "Once the new drug is in pharmacy, the physician may, as part of the practice of medicine vary the condition of use from those approved in the package insert, without obtaining approval of the FDA" as per The Federal Registrar, Vol. 37, No. 158, Aug. 15, 1972. This is clearly restated in the April 1982 FDA Drug Bulletin. Careful perusal of the current IND document also makes this clear. (Food and Drug Administration, HHS, Part 312-Investigational New Drug Application). As a therapy of blindness, the present invention advantageously comprises a new application of an established drug that can be immediately used with zero tolerance to time. This will be life saving and prevent malpractice risk. The risk management involves carefully monitoring adverse effects in the patient and discontinuing the drug if adverse effects are observed.

A practical application of the technology described herein may be found in the following exemplary case study.

Clinical Summary: MS K Oct. 25, 2023 Problem 1 Eye Disorder:

Pt has history of:

A. Uveitis history of >10 years back treated by Dr Y, specialist in immunity and Ophthalmologist B. Glaucoma: History of >10 years. Treated by Dr Y C. Cataract surgery: Rt Eye in past by Dr Y. (06/2018)

D. July 2023: Preoperative clearance for left eye cataract surgery by Dr Z, E. Jul. 20, 2023: Left Eye cataract surgery by Dr Y F. Jul. 20, 2023: Post cataract complications: lens ruptured posterior capsule. Dr Explained inadequate pupil dilation leading to complications.

G. Jul. 21, 2023: Referred pt to Dr V: Post cataract left eye surgery-lens displaced posteriorly Vitreo-retinal Consultants Advised wait before removing lens due to corneal oedema—may take 6 weeks and then schedule surgery. Dr Going on vacation for few weeks. Rx with? Eye drops H. Jul. 22, 2023: Second opinion sought with Dr A, I. July 23?: Adv to see Dr N, First to assess corneal oedema, Corneal Transplant surgeon to assess corneal swelling. Opined corneal swelling present may require corneal transplant in future.

J. July 24: Dr A: Aggressive treatment with prednisone eye drops to reduce swelling and once swelling reduced surgery will be done ASAP.

K. Aug. 16, 2023: Pt operated in 2-3 weeks time (see Maehara H. et al, "Tear fluid and complement activation products in tears after ocular surgery," BMC Ophthalmology, 2023, 23:329, the entire contents of which are incorporated herein by referenced thereto.)

L. Follow up appointments; weekly×3 then every three 3 weeks: 3 meetings completed.

Discussions during meetings: Retina tear/Blood collection/cloudy cornea initially after surgery.

As the time passed: Retina healed/bleeding cleared/eye sight slightly better

M. Refer to Dr N: ×2 times 3 weeks later

Discussions: Vision 20/200 Adv retina swelling need to subside, Plan? Split cornea transplant Risk mentioned 5% (This is true only for noninflammatory cornea conditions)

No urgency for surgery it can be delayed to January 2024.

N. Advised Glaucoma specialist to see on Nov. 30, 2023 Dr. H Recent Blood test 10/24/202: A1c 7.8; Bs 145 rest normal. Patient has following high risk factors for Cornea Transplant (see Armitage W. J., "High-risk Corneal Transplantation: Recent Developments and Future Possibilities," Transplantation, December 2019, Vol. 103, No. 12.) that increases the risk of corneal rejection to almost 50%.

1. H/o Blood transfusion: MVA 1987
2. H/o glaucoma
3. H/o Uveitis
4. Eye surgery
5. Surgery for complications of eye surgery
6. Diabetes/retinopathy
7. Aggressive use of immune suppressive and anti inflammatory drugs.

Figure 12:
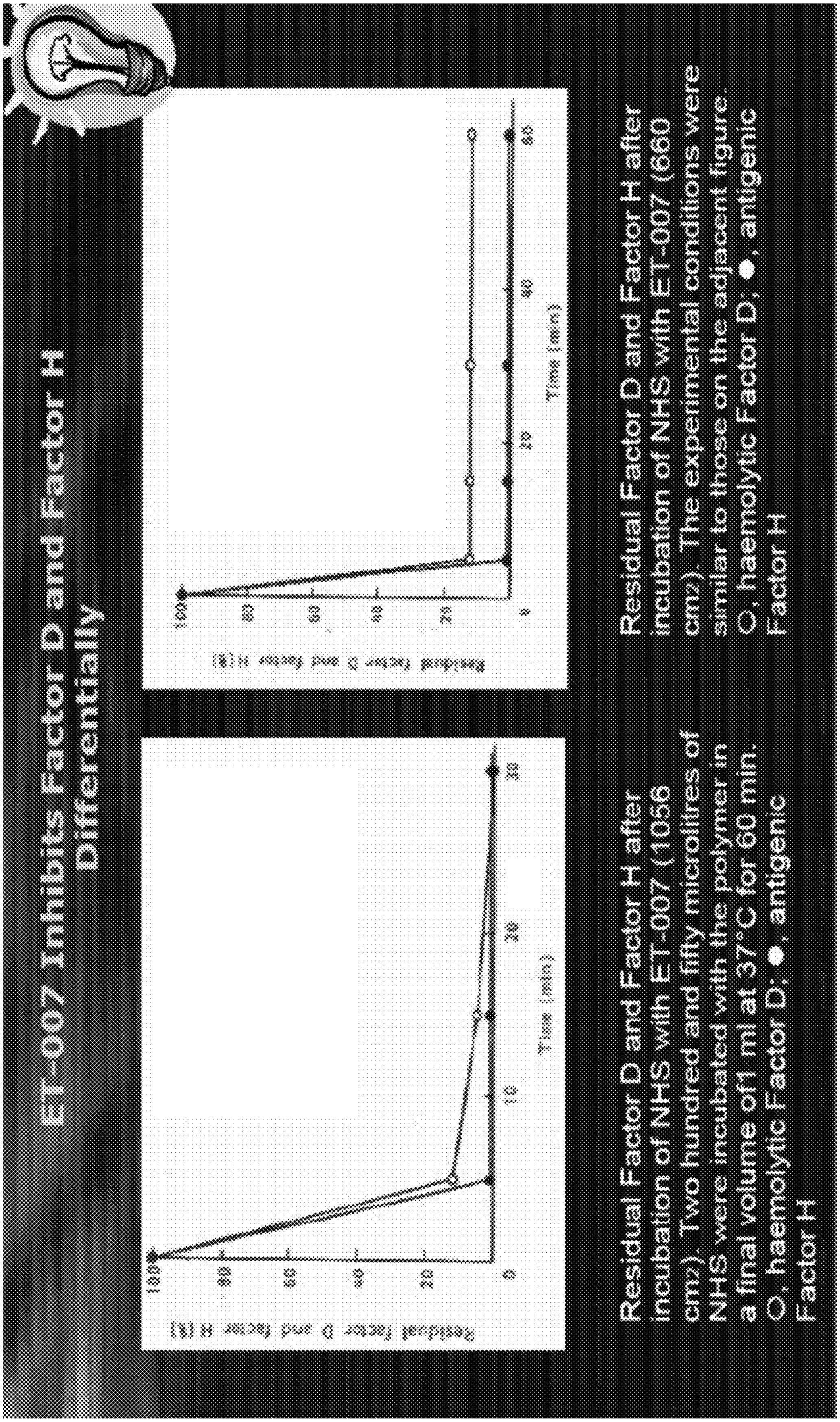
FIG. 12 is a pair of graphs showing how PSS inhibits Factor D and Factor H differently.
Figure 13:
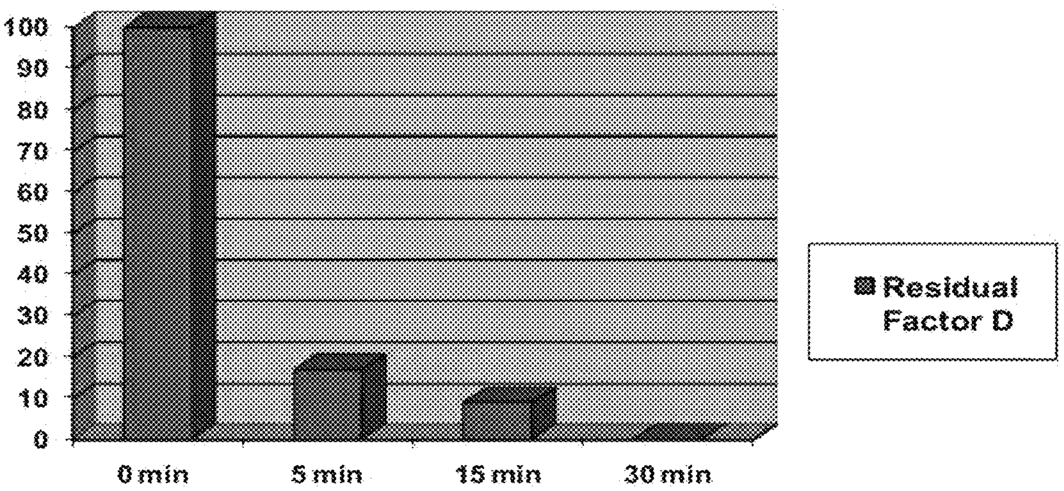
FIG. 13 is a graph showing residual Factor D levels over time.

Comments:

1. In the modern medical and surgical advances of "Eye Disorders" the missing element is "Complement Inhibitor" as shown in FIGS. 7-11. Specifically there is a need of Complement inhibitor of early complement system that can down regulate amplifying loop of complement that is modulation of Factor H, Factor D and Factor B as shown in FIGS. 12 & 13.
2. Early introduction of such advance are in keeping with "recent advances in Genomics and Fundamentals of Immunology."
3. It will reduce eye disorders at all stages of anterior chamber of eye disorders: viz Cornea cloudiness, uveitis, Lens problem and posterior chamber of eye disorders viz: Vitreous damage, retina damage, macular damage, diabetic retinopathy.
4. It will reduce excessive and aggressive use of immune suppressive and steroids and will help reduce the "High risk of Corneal Transplant."
5. It will reduce the risk of "Allo sensitization and risk or corneal transplant surgery.
6. Extensive human safety record and implementation of "Right to Try Law" is the fastest way globally to provide "prophylaxis and therapy of Blindness."
7. Our research and development methodology is summarized in FIG. 6.
8. How complement system activation contributes to explosive inflammation inside eye is shown in the educational video link https://www.youtube.com/watch?v=BSypUV6QUNw&t=6s.

Further Observations on High Risk Corneal Implants.

The basic concept that eye is an Immune privileged site and therefore success rate of whole/split corneal transplant is 95% is outdated concept and applies only in "Non inflammatory Corneal Transplants."

High risk Corneal Transplant is a condition where the immune privileged status of eyes is lost and therefore it has same risk as any other organ transplants.

There are several high risk predictors of "High Risk Corneal Transplants.

Risk Factors For High Risk Corneal Transplant

1. Glaucoma History: History of Glaucoma is the highest risk factor irrespective of intra ocular pressure: USA Cornea study reports rate of Corneal Transplant failure over 4 years is 55% if there was history of Glaucoma.
2. History of Inflammation/Steroid Use: The risk of failure in high risk corneal transplant is 58%.
3. The risk of whole vs split corneal transplant are inadequately studied.
4. Additional risk factors: Prior History of Blood transfusion/Surgery/Surgical Complications/Lens Status
5. In "High Risk Corneal Transplant rejection rate is 70% irrespective of Local or systemic steroid use and immune suppressive.

Although illustrative embodiments of the present invention have been described herein with reference to the accompanying drawings, it is to be understood that the present invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for therapy for complement-mediated hyper-inflammatory ocular diseases comprising:

formulating a polystyrene sulfonate based pharmacological composition selected from the group consisting of fractional purified sodium polystyrene sulfonate, fractional purified calcium polystyrene sulfonate, and combinations thereof;

forming the pharmacological composition into a gel;

selecting a patient suffering from a complement-mediated hyper-inflammatory ocular disease; and administering the pharmacological composition to the patient, wherein the pharmacological composition selectively targets key proteins involved in the C3 amplification loop to provide therapy for the complement-mediated hyper-inflammatory ocular disease.

2. The method according to claim 1, wherein the complement-mediated hyper-inflammatory ocular diseases are diseases occurring on the surface of the sclera or cornea.

3. The method according to claim 1, wherein the complement-mediated hyper-inflammatory ocular diseases are diseases selected from the group consisting of diseases of the tear fluid, anterior segment, iris, choroid, ciliary body, aqueous humor, posterior segments of the eye, vitreous humor or and retina.

4. The method according to claim 1, wherein the complement-mediated hyper-inflammatory diseases are diseases selected from the group consisting of diseases caused by trauma, surgery, implant of lens, transplant of cornea, laser therapy of retina, Diabetic retinopathy, retinitis pigmentosa or and age related macular degeneration (AMD).

5. The method of claim 1, wherein use of the pharmacological composition includes use to prevent progression of the complement mediated hyper inflammation and its progression of the disease to blindness.

6. The method according to claim 1, wherein the pharmacological composition selectively targets key proteins involved in the C3 amplification loop, wherein the key proteins are selected from the group consisting of Factor B, Factor D, Factor H, or its amplifying proteins of classical based systems, proteins of lectin based systems, or combinations thereof.

7. The method of claim 1, wherein the pharmacological composition is administered in an effective dosage in combination with ocular drugs.

* * * * *